US007204986B2

(12) United States Patent
Cheung

(10) Patent No.: US 7,204,986 B2
(45) Date of Patent: *Apr. 17, 2007

(54) METHOD TO PREPARE COMPOSITIONS COMPRISING YEAST TREATED WITH ELECTROMAGNETIC ENERGY

(75) Inventor: Ling Yuk Cheung, Hong Kong (HK)

(73) Assignee: Ultra Biotech Limited, Douglas (GB)

( * ) Notice: Subject to any disclaimer, the term of this patent is extended or adjusted under 35 U.S.C. 154(b) by 309 days.

This patent is subject to a terminal disclaimer.

(21) Appl. No.: 10/460,246

(22) Filed: Jun. 11, 2003

(65) Prior Publication Data

US 2004/0253251 A1   Dec. 16, 2004

(51) Int. Cl.
A61K 36/06 (2006.01)
A01N 63/04 (2006.01)
C12N 1/00 (2006.01)

(52) U.S. Cl. .............. 424/195.16; 424/725; 435/254.2
(58) Field of Classification Search .......... 424/195.16, 424/725; 435/245.2, 254.2
See application file for complete search history.

(56) References Cited

U.S. PATENT DOCUMENTS

| | | | |
|---|---|---|---|
| 2,107,830 A | 2/1938 | Liebesny et al. | |
| 3,711,392 A | 1/1973 | Metzger | |
| 3,870,599 A | 3/1975 | Azarowicz | |
| 3,903,307 A | 9/1975 | Kimura | |
| 3,968,254 A | 7/1976 | Rhodes et al. | |
| 4,041,182 A | 8/1977 | Erickson et al. | |
| 4,055,667 A | 10/1977 | Linton et al. | |
| 4,348,483 A | 9/1982 | Skogerson | |
| 4,582,708 A | 4/1986 | Tipton et al. | |
| 5,082,936 A | 1/1992 | James et al. | |
| 5,504,079 A | 4/1996 | James et al. | |
| 5,578,486 A | 11/1996 | Zhang | |
| 5,624,686 A | 4/1997 | Shimoda et al. | |
| 5,952,020 A | 9/1999 | Lizak | |
| 5,981,219 A | 11/1999 | Weber et al. | |
| 6,143,731 A | 11/2000 | James et al. | |
| 6,159,510 A | 12/2000 | Lizak | |
| 6,197,295 B1 | 3/2001 | Hsia et al. | |
| 6,214,337 B1 | 4/2001 | Hayen et al. | |
| 6,391,619 B1 | 5/2002 | Cheung | |
| 6,416,982 B1 | 7/2002 | Zhang | |
| 6,984,507 B2 * | 1/2006 | Cheung | 435/173.1 |
| 6,984,508 B2 * | 1/2006 | Cheung | 435/173.1 |
| 6,987,012 B2 * | 1/2006 | Cheung | 435/173.1 |
| 6,989,253 B2 * | 1/2006 | Cheung | 435/173.1 |
| 2002/0099026 A1 | 7/2002 | Goodman et al. | |

FOREIGN PATENT DOCUMENTS

| | | |
|---|---|---|
| CN | 1110317 | 10/1995 |
| CN | 1 207 873 | 2/1999 |
| EP | 553 777 | 8/1993 |
| ES | 475500 | 11/1978 |
| FR | 2 222 433 | 10/1974 |
| JP | 60 028893 | 2/1985 |
| SU | 1 071 637 | 2/1984 |
| SU | 1722364 | 3/1992 |
| SU | 1750570 | 7/1992 |
| WO | WO 87/02705 | 5/1987 |
| WO | WO 95/04814 | 2/1995 |
| WO | WO 02/20431 | 3/2002 |
| WO | WO 02/062981 | 8/2002 |
| WO | WO 02/062982 | 8/2002 |
| WO | WO 02/062983 | 8/2002 |
| WO | WO 02/062984 | 8/2002 |
| WO | WO 02/062985 | 8/2002 |
| WO | WO 02/070436 | 9/2002 |
| WO | WO 02/070683 | 9/2002 |

OTHER PUBLICATIONS

Dutta et al. Journal of Microwave Power. 1979. vol. 14, No. 3, pp. 275-280.*
U.S. Appl. No. 10/175,058, filed Jun. 18, 2002, Cheung L.Y.
U.S. Appl. No. 10/175,053, filed Jun. 18, 2002, Cheung L.Y.
U.S. Appl. No. 10/175,054, filed Jun. 18, 2002, Cheung L.Y.
U.S. Appl. No. 10/175,010, filed Jun. 18, 2002, Cheung L.Y.
U.S. Appl. No. 10/175,055, filed Jun. 18, 2002, Cheung L.Y.
U.S. Appl. No. 10/460,323, filed Jun. 11, 2003, Cheung L.Y.
U.S. Appl. No. 10/460,338, filed Jun. 11, 2003, Cheung L.Y.
U.S. Appl. No. 10/184,749, filed Jun. 28, 2002, Cheung L.Y.
U.S. Appl. No. 10/175,052, filed Jun. 18, 2002, Cheung L.Y.
U.S. Appl. No. 10/175,051, filed Jun. 18, 2002, Cheung L.Y.
U.S. Appl. No. 10/175,049, filed Jun. 18, 2002, Cheung L.Y.
U.S. Appl. No. 10/175,050, filed Jun. 18, 2002, Cheung L.Y.
U.S. Appl. No. 10/175,056, filed Jun. 18, 2002, Cheung L.Y.
U.S. Appl. No. 10/175,014, filed Jun. 18, 2002, Cheung L.Y.
U.S. Appl. No. 10/175,016, filed Jun. 18, 2002, Cheung L.Y.
U.S. Appl. No. 10/175,015, filed Jun. 18, 2002, Cheung L.Y.
U.S. Appl. No. 10/610,578, filed Jun. 30, 2003, Cheung L.Y.
U.S. Appl. No. 10/460,324, filed Jun. 11, 2003, Cheung L.Y.
U.S. Appl. No. 10/460,530, filed Jun. 11, 2003, Cheung L.Y.
U.S. Appl. No. 10/460,271, filed Jun. 11, 2003, Cheung L.Y.
U.S. Appl. No. 10/460,341, filed Jun. 11, 2003, Cheung L.Y.
U.S. Appl. No. 10/460,337, filed Jun. 11, 2003, Cheung L.Y.
U.S. Appl. No. 10/460,326, filed Jun. 11, 2003, Cheung L.Y.
U.S. Appl. No. 10/460,327, filed Jun. 11, 2003, Cheung L.Y.
U.S. Appl. No. 10/460,325, filed Jun. 11, 2003, Cheung L.Y.
U.S. Appl. No. 10/460,832, filed Jun. 11, 2003, Cheung L.Y.

(Continued)

Primary Examiner—Jon Weber
Assistant Examiner—Kailash C. Srivastava
(74) Attorney, Agent, or Firm—Jones Day

(57) ABSTRACT

The present invention relates to pharmaceutical compositions and dietary supplement comprising yeast cells that can produce a healthful benefit in a subject inflicted with ovarian cancer. The biological compositions can be used to retard the growth of ovarian cancer cells and/or prolonging the time of survival of the subject. The invention also relates to methods for manufacturing the biological compositions.

8 Claims, 2 Drawing Sheets

OTHER PUBLICATIONS

Figure 1:
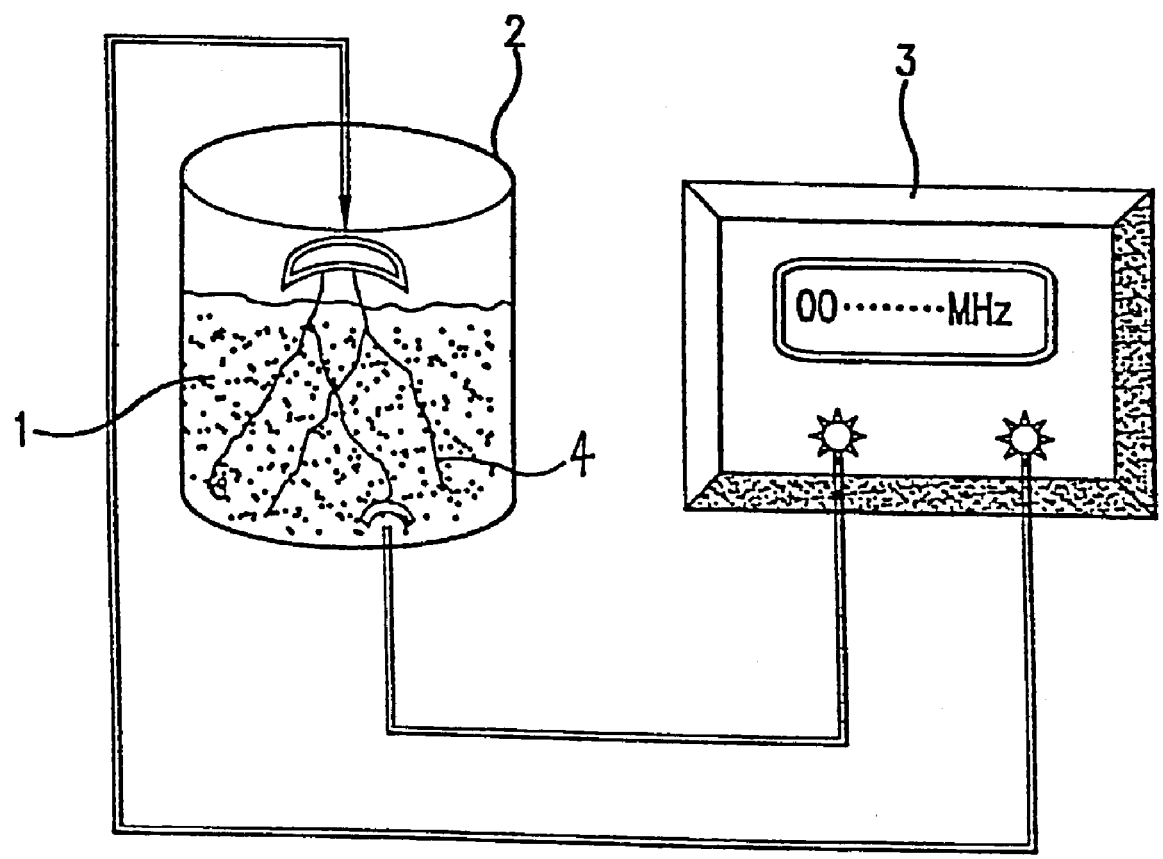

U.S. Appl. No. 10/460,336, filed Jun. 11, 2003, Cheung L.Y.
U.S. Appl. No. 10/460,833, filed Jun. 11, 2003, Cheung L.Y.
U.S. Appl. No. 10/460,437, filed Jun. 11, 2003, Cheung L.Y.
U.S. Appl. No. 10/460,328, filed Jun. 11, 2003, Cheung L.Y.
U.S. Appl. No. 10/460,438, filed Jun. 11, 2003, Cheung L.Y.
U.S. Appl. No. 10/460,247, filed Jun. 11, 2003, Cheung L.Y.
U.S. Appl. No. 10/185,276, filed Jun. 28, 2002, Cheung L.Y.
Lin H. et al. 1994. Specific region of the c-myc promoter is responsive to electric and magnetic fields. J Cell Biochem. 54(3):281-288.
Lin H. et al. 1999. A magnetic field-responsive domain in the human HSP70 promoter. J Cell Biochem. 75:170-176.
Machado et al. 1986. Immunopharmacological effects of *Saccharomyces boulardii* in healthy human volunteers. Int'l Immunology and Immunopathology (United Kingdom). 8(3):245-259.
Moore RL. 1979. Biological effects of magnetic fields : studies with microorganisms. Can. J. Microbiol. 25:1145-1151.
Norris et al. 1997. Do bacteria sing? Sonic intercellular communication between bacteria may reflect electromagnetic intracellular communication involving coherent collective vibrational modes that could integrate enzyme activities and gene expression. Mol Microbiol. 24(4):879-80.
Ortuno et al. 2002. Oral administration of yeast, *Saccharomyces cerevisiae*, enhances the cellular innate immune response of gilthead seabream (*Sparus aurata L.*). Vet Immunol Immunopathol. (Netherlands) 85(1-2):41-50.
Phillips JL. 1993. Effects of electromagnetic field exposure on gene transcription. J Cell Biochem. 51(4):381-386.
Pichiko et al. 1996. Electromagnetic stimulation of productivity of microorganisms and its mechanisms. Prikladnaya Biokhimiya I Mikrobiologiya 32(4):468-472.
Ponne et al. 1995. Interaction of electromagnetic energy with biological material—relation to food processing. Radiation Physics and Chemistry, 45(4):591-607.
Romano-Spica et al. 2000. Ets1 oncogene induction by ELF-modulated 50 MHz radiofrequency electromagnetic field. Bioelectromagnetics. 21(1):8-18.
Saha et al. 1999. Microbial Manipulation of Rumen Fermentation Using *Saccharomyces cerevisiae* as Probiotics. Current Science (Bangalore) 77(5):696-697.
Van Rensburg et al. 1998. Engineering yeast for efficient cellulose degradation. Yeast. 14(1):67-76.
Zhang et al. 1992. Electrostimulation of the dehydrogenase system of yeast by alternating currents. Bioelectrochemistry and Bioenergetics 28:341-353.

Zhang LY. 1994. Introduction to TLB, A Complex Microbial Fertilizer- Preliminary Application of MAB in Agriculture. *Academic Theses on TLB Complex Microbial Fertilizer*. Zhang, LY. eds. China Science and Technology Press. pp. 1-17 (with English Abstract).
1992 China Catalogue of Cultures, China Machine Press, Beijing, China, 1992, pp. I-XV and 164-185.
Bassett CA. 1993. Beneficial effects of electromagnetic fields. J Cell Biochem. 51(4):387-393.
Binninger et al. 1997. Effects of 60Hz AC magnetic fields on gene expression following exposure over multiple cell generations using *Saccharomyces cerevisiae*. Bioelectrochemistry and Bioenergetics 43(1):83-89.
Born et al. 1993. *Saccharomyces boulardii* therapy of HIV associated features (2). Deutsche Medizinische Wochenschrift (Germany) 118(2):765.
Filho et al. 1998. Dose effect of oral *Saccharomyces boulardii* treatments on morbidity and mortality in immunosuppressed mice. J Med Microbio. (United Kingdom) 47(2):111-116.
Gonzalez et al. 1980. Effects of an electric field of sinusoidal waves on the amino acid biosynthesis by *Azotobacter*. Z. Naturforsch. 35c:258-261.
Goodman et al. 1995. Effects of electromagnetic fields on molecules and cells. *International Review of Cytology*. Eds. Kwang et al. Academic Press vol. 158, pp. 279-339.
Goodman et al. 1998. Magnetic field stress induces expression of *hsp70*. Cell Stress & Chaperones. 3(2):79-88.
Grospietsch et al. 1995. Stimulating effects of modulated 150 MHz electromagnetic fields on the growth of *Escherichia coli* in a cavity resonator. Bioelectrochemistry and Bioenergetics. 37:17-23.
Grundler et al. Mechanisms of electromagnetic interaction with cellular systems. Naturwissenschafter 79:551-559, 1992.
Grundler et al. 1982. Resonant-like dependence of yeast growth rate on microwave frequencies. Br J Cancer Suppl. 45(5):206-208.
Grundler W. 1978. Nonthermal effects of millimeter microwaves on yeast growth. Z. Naturforsch. 33c:15-22.
Grundler W. 1989. Resonant microwave effect on locally fixed yeast microcolonies. Z. Naturforsch. 44c:863-866.
Kim et al. 2001. Anti-stress and anti-fatigue effects of fermented rice bran. Biosci Biotechnol Biochem. 65(10):2294-2296.

* cited by examiner

METHOD TO PREPARE COMPOSITIONS COMPRISING YEAST TREATED WITH ELECTROMAGNETIC ENERGY

1. FIELD OF THE INVENTION

The invention relates to oral compositions comprising yeast cells that can produce a healthful benefit in a subject inflicted with ovarian cancer. The invention also relates to methods for manufacturing the oral compositions and methods of use thereof.

2. BACKGROUND OF THE INVENTION

2.1 Ovarian Cancer

Ovarian cancer is the third most common malignant tumor and the fifth leading cause of cancer death in women. Only 39% of all women with ovarian cancer survive for 5 years. Ovarian cancer is a deadly disease that accounted for about 13,600 deaths in the United States in 1994 as well as some 24,000 new cases (Boring et al., 1994, *CA Cancer J. Clin.* 44:7–26). Ovarian cancer is more common in industrialized nations, with the exception of Japan. The average age of diagnosis of women with ovarian cancer is almost 60. The incidence of ovarian cancer is 16 per 100,000 women who are 40 years of age and old. This number increases to 56 per 100,000 women who are 70 years of age and older. More than half of the deaths from ovarian cancer occur in women between 55 and 74 years of age. Approximately one quarter of ovarian cancer deaths occur in women between 35 and 54 years of age.

There are several well recognized risk factors for ovarian cancer. Older women have a higher risk of developing ovarian cancer. The more children a woman has, the lower her risk of ovarian cancer. Early age at first pregnancy and the use of oral contraceptive pills have also been shown to have a protective effect. In contrast, the use of fertility drugs has been associated with an increased chance of developing ovarian cancer. Family history is the single most important risk factor for the development of ovarian cancer. Those with breast cancer also are at higher risk. Ovarian cancer in two or more first-degree relatives (mother or sister) suggests a hereditary cause. A family history of colon, lung, prostate, and uterine cancers may indicate the presence of a Lynch II syndrome, which may also confer a higher risk for developing ovarian cancer. White women are about 70 percent more likely than black women to get ovarian cancer (Parazzini et al., 1991, *Gynecol Oncol.* 41:1–16). Other factors include talc use, asbestos exposure, early menstruation or menopause, high dietary fat content, and childhood mumps infection are controversial and have not been definitively proven.

The symptoms of ovarian cancer are vague and nonspecific. Common symptoms include abdominal pain, abdominal swelling, bloating or dyspepsia, pelvic pressure, weight gain or loss, abnormal menstrual cycles, increased abdominal girth, vaginal bleeding, excessive hair, and increased urinary frequency or urgency. In 60% to 70% of the patients, by the time the cancer is diagnosed, the tumor has often spread beyond the ovaries. Ovarian cancers shed malignant cells which frequently implant on the uterus, bladder, bowel, and omentum and often begin forming new tumor growths before cancer is even suspected. Currently used screening tests include CBC, blood chemistry, CA125, quantitative serum HCG (blood pregnancy test), alpha fetoprotein (AFP), urinalysis, GI series, laparotomy exploratory, ultrasound, abdominal CT scan or MRI. Unfortunately, the only sure way to know is by biopsy. Over 50 percent of women with ovarian cancer are diagnosed in the advanced stages of the disease.

Ovarian neoplasms are classified according to cell of origin. There are three major types of ovarian cancer, those arising from the celomic epithelium (60% to 70% of cases), specialized stroma (5% to 10%), and germ cell layer (or unfertilized ovum) (15% to 20%). The most common ovarian tumor is serous carcinoma, which tends to grow rapidly with early intraperitoneal spread.

The staging of ovarian cancer is based on the revised criteria of TNM staging by the American Joint Committee for Cancer (AJCC) published in 1988. Staging is the process of describing the extent to which cancer has spread from the site of its origin. It is used to assess a patient's prognosis and to determine the choice of therapy. The stage of a cancer is determined by the size and location in the body of the primary tumor, and whether it has spread to other areas of the body. Staging involves using the letters T, N and M to assess tumors by the size of the primary tumor (T); the degree to which regional lymph nodes (N) are involved; and the absence or presence of distant metastases (M)—cancer that has spread from the original (primary) tumor to distant organs or distant lymph nodes. Each of these categories is further classified with a number 1 through 4 to give the total stage. Once the T, N and M are determined, a "stage" of I, II, III or IV is assigned. Stage I cancers are small, localized and usually curable. Stage II and III cancers typically are locally advanced and/or have spread to local lymph nodes. Stage IV cancers usually are metastatic (have spread to distant parts of the body) and generally are considered inoperable.

Treatment options for ovarian cancer include surgery, radiation therapy, hormone therapy, chemotherapy, and vaccines comprising monoclonal antibodies that blocks growth-factor receptors on the surface of cancer cells and thereby, preventing the activation and growth of cancer cells. Surgery is the most common treatment for ovarian cancer and involves removing the ovary as well as some tissue surrounding it. During the surgery, a sample of the lymph nodes in nearby tissue is usually removed to better assess whether the cancer has spread beyond the ovary. Survival has been shown to correlate strongly with residual disease. Aure and coworkers reported improvements in the 5-year survival of Stage II patients (from 18% to 55%) and Stage III patients (from 8% to 30%) who were optimally resected. (1971, *Obstet Gynecol.* 37:1) However, one permanent side effect of surgery is infertility.

Radiation therapy is the second most common treatment. For the treatment of ovarian cancer, the high-energy rays can be delivered by two basic methods: external beam (similar to an x-ray) or brachytherapy (internal radiation delivered with implanted radioactive seeds). Fatigue is a possible side effect of radiation therapy, but it gradually ceases after treatment is completed. Some women may also experience bowel problems, urinary problems, and rectal discomfort or bleeding. Depending on how extensive the cancer is or how big the tumor has grown, hormone therapy may be used before radiation therapy to help shrink the size of the tumor, thereby making it easier to treat. Hormone therapy decreases the amount of the male hormone testosterone in the body, which can promote the growth of cancer cells.

Chemotherapy is used primarily in cases where the disease has spread outside the ovary and where hormonal treatments alone are no longer effective in preventing tumor growth. Potential side effects include nausea and vomiting, loss of hair, low blood cell counts, and fatigue. Many chemotherapeutic drugs have been tried in the past as single agents for the palliation of ovarian cancer, but the results were generally disappointing. Nevertheless, the role of chemotherapy in the management of ovarian cancer is continually evolving. Oftentimes, chemotherapy with radiation in adjunct to surgery is used. In general, chemotherapy can achieve long-term survival rates of up to 15% to 20%, even in patients with recurrent or metastatic disease (Ali et al., 2000, *Oncology* 14(8):1223–30). Unfortunately, the high initial response rates to first line chemotherapy does not appear to translate into a survival benefit (Kohno and Kitahara, 2001, Gan To Kagaku Ryoho 28(4):448–53). Moreover, there are many undesirable side effects associated with chemotherapy such as temporary hair loss, mouth sores, anemia (decreased numbers of red blood cells that may cause fatigue, dizziness, and shortness of breath), leukopenia (decreased numbers of white blood cells that may lower resistance to infection), thrombocytopenia (decreased numbers of platelets that may lead to easy bleeding or bruising), and gastrointestinal symptoms like nausea, vomiting, and diarrhea. Active chemotherapeutic agents include mitoxantrone, prednisone, paclitaxel, docetaxel, estramustine, adriamycin, estramustine phosphate (Emcyt®), and mitoxantrone (Novantrone®).

The identification of active chemotherapeutic agents against cancers traditionally involved the use of various animal models of cancer. The mouse has been one of the most informative and productive experimental system for studying carcinogenesis (Sills et al., 2001, *Toxicol Letters* 120:187–198), cancer therapy (Malkinson, 2001, *Lung Cancer* 32(3):265–279; Hoffman RM., 1999, *Invest New Drugs* 17(4):343–359), and cancer chemoprevention (Yun, 1999, *Annals NY Acad Sci.* 889:157–192). Cancer research started with transplanted tumors in animals which provided reproducible and controllable materials for investigation. Pieces of primary animal tumors, cell suspensions made from these tumors, and immortal cell lines established from these tumor cells propagate when transplanted to animals of the same species.

To transplant human cancer to an animal and to prevent its destruction by rejection, the immune system of the animal are compromised. While originally accomplished by irradiation, thymectomy, and application of steroids to eliminate acquired immunity, nude mice that are athymic congenitally have been used as recipients of a variety of human tumors (Rygaard, 1983, in 13$^{th}$ International Cancer Congress Part C, Biology of Cancer (2), pp37–44, Alan R. Liss, Inc., NY; Fergusson and Smith, 1987, *Thorax,* 42:753–758). While the athymic nude mouse model provides useful models to study a large number of human tumors in vivo, it does not develop spontaneous metastases and are not suitable for all types of tumors. Next, the severe combined immunodeficient (SCID) mice is developed in which the acquired immune system is completely disabled by a genetic mutation. Human lung cancer was first used to demonstrate the successful engraftment of a human cancer in the SCID mouse model (Reddy S., 1987, *Cancer Res.* 47(9):2456–2460). Subsequently, the SCID mouse model have been shown to allow disseminated metastatic growths for a number of human tumors, particularly hematologic disorders and malignant melanoma (Mueller and Reisfeld, 1991, *Cancer Metastasis Rev.* 10(3): 193–200; Bankert et al., 2001, *Trends Immunol.* 22:386–393). With the recent advent of transgenic technology, the mouse genome has become the primary mammalian genetic model for the study of cancer (Resor et al., 2001, *Human Molec Genet.* 10:669–675).

While surgery, chemotherapeutic agents and radiation are useful in the treatment of ovarian cancer, there is a continued need to find better treatment modalities and approaches to manage the disease that are more effective and less toxic, especially when clinical oncologists are giving increased attention to the quality of life of cancer patients. The present invention provides an alternative approach to cancer therapy and management of the disease by using an oral composition comprising yeasts.

2.2 Yeast-Based Compositions

Yeasts and components thereof have been developed to be used as dietary supplement or pharmaceuticals. However, none of the prior methods uses yeast cells which have been cultured in an electromagnetic field to produce a product that has an anti-cancer effect. The following are some examples of prior uses of yeast cells and components thereof:

U.S. Pat. No. 6,197,295 discloses a selenium-enriched dried yeast product which can be used as dietary supplement. The yeast strain *Saccharomyces boulardii* sequela PY 31 (ATCC 74366) is cultured in the presence of selenium salts and contains 300 to about 6,000 ppm intracellular selenium. Methods for reducing tumor cell growth by administration of the selenium yeast product in combination with chemotherapeutic agents is also disclosed.

U.S. Pat. No. 6,143,731 discloses a dietary additive containing whole β-glucans derived from yeast, which when administered to animals and humans, provide a source of fiber in the diet, a fecal bulking agent, a source of short chain fatty acids, reduce cholesterol and LDL, and raises HDL levels.

U.S. Pat. No. 5,504,079 discloses a method of stimulating an immune response in a subject utilizing modified yeast glucans which have enhanced immunobiologic activity. The modified glucans are prepared from the cell wall of *Saccharomyces* yeasts, and can be administered in a variety of routes including, for example, the oral, intravenous, subcutaneous, topical, and intranasal route.

U.S. Pat. No. 4,348,483 discloses a process for preparing a chromium yeast product which has a high intracellular chromium content. The process comprises allowing the yeast cells to absorb chromium under a controlled acidic pH and, thereafter inducing the yeast cells to grow by adding nutrients. The yeast cells are dried and used as a dietary supplement.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

3. SUMMARY OF THE INVENTION

The present invention relates to biological or oral compositions useful for subjects with ovarian cancer. In one embodiment, the present invention provides biological compositions comprising live yeast cells which are capable of producing a healthful benefit in subjects with ovarian cancer. In other embodiments, the invention provides methods of making the biological compositions, and methods of using the biological compositions.

In particular, the methods of the invention comprise culturing yeast cells in the presence of a series of electromagnetic fields such that the yeast cells becomes metabolically active. The electromagnetic fields used are each defined by one of five frequency ranges and a broad range of field strength. The starting yeast cells are commercially available and/or accessible to the public, such as but not limited to *Saccharomyces*. The methods for making the biological compositions of the invention further comprise conditioning the activated yeast cells in plant extracts and the gastric juice of animals, while in the presence of another series of electromagnetic fields.

The methods of manufacturing also comprise expanding the number of activated or activated and conditioned yeast cells in large scale cultures in the presence of yet another series of electromagnetic fields, performing quality control measures, and packaging. Pharmaceutical compositions of the invention comprises activated and conditioned yeast cells and one or more pharmaceutically acceptable excipients or carriers. Additional ingredients, such as vitamins and/or flavors may be added to the biological compositions to form the oral compositions of the invention. Such additional carriers and ingredients can improve the healthful benefits, pharmacological properties, and organoleptic characteristics of the oral compositions. During the manufacturing process, the activated or activated and conditioned yeast cells may be dried and stored for a period of time.

The biological or oral compositions of the invention are ingested by the subject or used as an additive to be incorporated into food to be consumed by the subject. Dietary supplement and nutritional compositions comprising activated and conditioned yeast cells are encompassed by the invention. Preferably, the subject is a human being.

In various embodiments, the biological or oral compositions of the invention are used to produce a healthful benefit in a subject with ovarian cancer or at high risk of developing ovarian cancer. In particular, the biological composition of the invention can retard the growth of ovarian cancer cells in an animal which received the composition orally. The composition can also be used to prolong the time of survival of an animal with ovarian cancer.

4. BRIEF DESCRIPTION OF FIGURES

FIG. 1 Activation and conditioning of yeast cells. 1 yeast cell culture; 2 container; 3 electromagnetic field source; 4 electrode.

Figure 2:
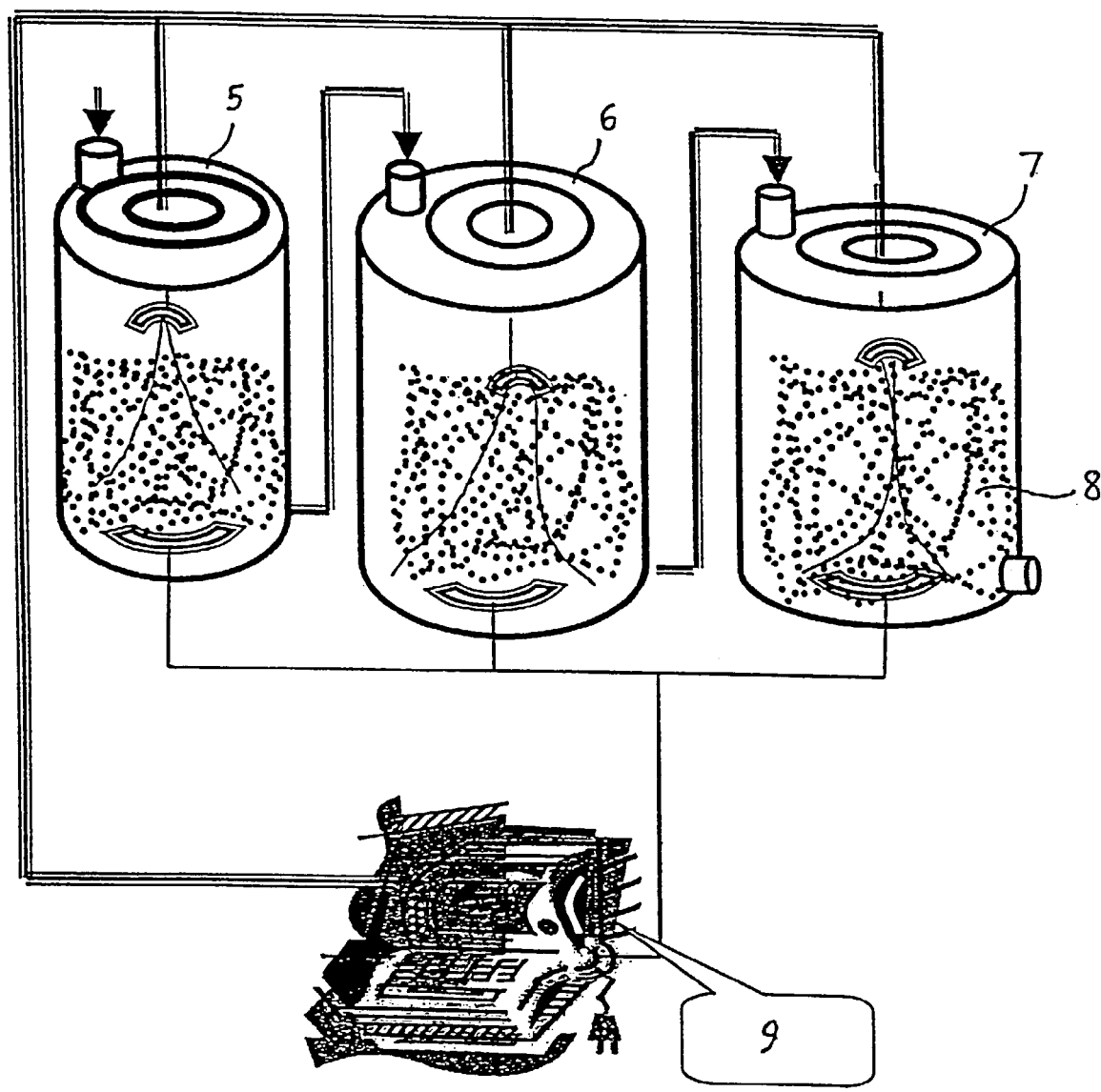

FIG. 2 Large scale propagation of yeast cells. 5 first container; 6 second container; 7 third container; 8 yeast cell cultures; 9 electromagnetic field source.

5. DETAILED DESCRIPTION OF THE INVENTION

The present invention relates to biological compositions that can produce a healthful benefit in a subject with ovarian cancer. The present invention provides methods for manufacturing the biological compositions as well as methods for using the biological compositions.

In one embodiment, the invention provides biological compositions that comprise yeasts. Unlike the traditional use of yeasts in the making of food, the yeast cells of the invention are not used as a source of enzymes that acts on the food ingredients. The yeasts are not a primary source of nutrients for the subject. Nor are yeast cells used as a carrier, such as metal salts. The yeast cells of the invention are live when administered orally or ingested along with food by a subject. Without being bound by any theory or mechanism, the inventor believes that the culture conditions activate and/or amplified the expression of a gene or a set of genes in the yeast cells such that the yeast cells becomes highly effective in stimulating the animal's immune system, including both specific and non-specific immunological reactions, the results of which are manifested as the overall healthful benefits observed in the treated subject. The healthful benefits provided by using the biological compositions are demonstrated in animal models of human ovarian cancer which show inhibition of tumor growth and prolonged survival time of animals with the disease.

In another embodiment, the invention provides methods for making the yeast cells in the biological compositions. The starting materials are normal yeast cells which can be readily obtained commercially or from public microorganism deposits. The methods of the invention comprise a set of culture conditions that can be applied reproducibly to activate the yeast cells. The key feature of the culture conditions used in the methods of the invention is a series of alternating electromagnetic fields of defined frequency ranges and field strengths which are applied to the growing yeast cell culture. The method further comprises the step of conditioning the activated live yeast cells to the acidic environment of the stomach of the subject. The electromagnetic fields used in these methods can be created reproducibly at various scales, thus enabling even the large scale manufacturing of the biological compositions of the invention. By careful control of the culturing conditions, normal yeast cells can be activated routinely and reproducibly to become yeast cells of the invention.

In yet another embodiment, the invention provides methods for manufacturing an oral composition comprising activated and conditioned yeasts of the invention, and additional ingredients, including but not limited to pharmaceutically acceptable carriers or excipients, vitamins, herbs (including traditional Chinese medicine products), herbal extracts, minerals, amino acids, flavoring agents, coloring agents, and/or preservatives.

In yet another embodiment, the biological compositions can be added to food which will be consumed by the subject. As known to those skilled in the relevant art, many methods may be used to mix the biological or oral compositions of the invention with food while the yeast cells remain viable. In a particular embodiment, the culture broth comprising live yeast cells of the present invention are added directly to food just prior to consumption. Dried powders of the yeasts can also be reconstituted and added directly to food just prior to consumption.

In various embodiments, the oral compositions of the invention can be consumed directly by a subject or be fed directly to a subject. For example, the subject may drink the culture broth or a fraction thereof that comprises live activated and conditioned yeast cells. Oral compositions comprising dried yeast cells can also be given as a solid dosage form to the subject.

Although it is not necessary, the biological or oral compositions of the invention can be used in conjunction or in rotation with other types of treatment modalities such as but not limited to surgery, chemotherapeutic agents, and radiation. Since the biological compositions of the invention are administered orally, the assistance of health professionals in administration of the composition is generally not essential.

Described below in Section 5.1 are the yeast cells of the invention and methods of their preparation. Section 5.2 describes the use of the biological compositions of the invention in a subject suffering from ovarian cancer. The examples in Sections 6 to 9 demonstrate the therapeutic benefits of an oral composition of the invention. The activated and conditioned yeast cells in the oral composition are characterized by their ability to (i) suppress the growth of cancer cells in an animal model of human ovarian cancer, or (ii) prolong the survival of animals with transplanted cancer cells in a model of human ovarian cancer, as compared to yeast cells which have not been activated and conditioned.

5.1 Preparation of the Yeast Cell Cultures

The yeast cells of the biological composition are produced by culturing a plurality of yeast cells in an appropriate culture medium in the presence of an alternating electromagnetic field over a period of time. The method comprises a first step of activating the yeast cells and a second step of conditioning the activated yeast cells. The activation process comprises culturing yeast cells in the presence of at least two, three, four or five electromagnetic fields of specific frequencies and field strength. The conditioning process comprises further culturing of the activated yeast cells in a medium comprising plant extracts and extracts from the stomach of an animal, in the presence of at least one electromagnetic field. The activated and conditioned yeast cells can be stored as dried cells after drying the cells under appropriate conditions. The dried activated and conditioned yeast cells can be used later in large scale culturing processes for manufacturing the biological compositions of the invention. The various culturing processes of the invention can be performed either as a batch process or a continuous process.

5.1.1 Yeasts

In various embodiments, yeasts of the genera of *Saccharomyces, Candida, Crebrothecium, Geotrichum, Hansenula, Kloeckera, Lipomyces, Pichia, Rhodosporidium, Rhodotorula, Torulopsis, Trichosporon*, and *Wickerhamia* can be used in the invention. Generally, fungi used for food manufacturing are preferred.

Non-limiting examples of yeast strains include *Saccharomyces* sp., AS2.311; *Schizosaccharomyces pombe* Linder, AS2.214, AS2.248, AS2.249, AS2.255, AS2.257, AS2.259, AS2.260, AS2.274, AS2.994, AS2.1043, AS2.1149, AS2.1178, IFFI 1056; *Saccharomyces sake* Yabe, ACCC2045; *Saccharomyces uvarum Beijer*, IFFI 1023, IFFI 1032, IFFI 1036, IFFI 1044, IFFI 1072, IFFI 1205, IFFI 1207; *Saccharomyces rouxii* Boutroux, AS2.178, AS2.180, AS2.370, AS2.371; *Saccharomyces cerevisiae* Hansen Var. *ellipsoideus*, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces carlsbergensis* Hansen, AS2.116, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042; *Rhodotorula aurantiaca* (Saito)Ladder; AS2.102, AS2.107, AS2.278, AS2.499, AS2.694, AS2.703, AS2.704 and AS2.1146; *Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.14, AS2.16, AS2.56, AS2.69, AS2.70, AS2.93, AS2.98, AS2.101, AS2.109, AS2.110, AS2.112, AS2.139, AS2.173, AS2.182, AS2.196, AS2.242, AS2.336, AS2.346, AS2.369, AS2.374, AS2.375, AS2.379, AS2.380, AS2.382, AS2.393, AS2.395, AS2.396, AS2.397, AS2.398, AS2.399, AS2.400, AS2.406, AS2.408, AS2.409, AS2.413, AS2.414, AS2.415, AS2.416, AS2.422, AS2.423, AS2.430, AS2.431, AS2.432, AS2.451, AS2.452, AS2.453, AS2.458, AS2.460, AS2.463, AS2.467, AS2.486, AS2.501, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI 1001, IFFI 1002, IFFI 1005, IFFI 1006, IFFI 1008, IFFI 1009, IFFI 1010, IFFI 1012, IFFI 1021, IFFI 1027, IFFI 1037, IFFI 1042, IFFI 1045, IFFI 1048, IFFI 1049, IFFI 1050, IFFI 1052, IFFI 1059, IFFI 1060, IFFI 1062, IFFI 1202, IFFI 1203, IFFI 1209, IFFI 1210, IFFI 1211, IFFI 1212, IFFI 1213, IFFI 1215, IFFI 1221, IFFI 1224, IFFI 1247, IFFI 1248, IFFI 1251, IFFI 1270, IFFI 1277, IFFI 1289, IFFI 1290, IFFI 1291, IFFI 1292, IFFI 1293, IFFI 1297, IFFI 1300, IFFI 1301, IFFI 1302, IFFI 1307, IFFI 1308, IFFI 1309, IFFI 1310, IFFI 1311, IFFI 1331, IFFI 1335, IFFI 1336, IFFI 1337, IFFI 1338, IFFI 1339, IFFI 1340, IFFI 1345, IFFI 1348, IFFI 1396, IFFI 1397, IFFI 1399, IFFI 1441 and IFFI 1443. Preferred yeast strains include but are not limited to *S. cerevisiae* AS2.501, AS2.502, AS2.503, AS2.504, AS2.535, AS2.558, AS2.560, AS2.561 and AS2.562.

Generally, yeast strains useful for the invention can be obtained from private or public laboratory cultures, or publicly accessible culture deposits, such as the American Type Culture Collection, 10801 University Boulevard, Manassas, Va. 20110-2209 and the China General Microbiological Culture Collection Center (CGMCC), China Committee for Culture Collection of Microorganisms, Institute of Microbiology, Chinese Academy of Sciences, Haidian, P.O. Box 2714, Beijing, 100080, China.

Non-limiting examples of using yeast cells of the invention with *Saccharomyces cerevisiae* Hansen strain AS2.502 are provided in Sections 6 to 9 herein below. The yeast cells of the invention do not comprise an enhanced level of selenium or chromium relative to that found in naturally occurring yeast cells. In certain embodiments, the biological compositions do not comprise cells of *Saccharomyces boulardii* (for example, ATCC Accession No. 74366) or cells of a particular strain of *Saccharomyces cerevisiae* (strain Hansen CBS 5926) that is also commonly referred to as *Saccharomyces boulardii*.

Although it is preferred, the preparation of the yeast cells of the invention is not limited to starting with a pure strain of yeast. The yeast cells in the biological compositions may be produced by culturing a mixture of yeast cells of different species or strains. The constituents of a mixture of yeast cells can be determined by standard yeast identification techniques well known in the art.

In various embodiments of the invention, standard techniques for handling, transferring and storing yeasts are used. Although it is not necessary, sterile conditions or clean environments are highly desirable when carrying out the manufacturing processes of the invention, especially when the biological compositions are for human consumption. The manufacturing process can be adapted to meet regulatory guidelines on product safety and quality control by standard practice known in the art.

5.1.2 Electromagnetic Fields

As used herein, the terms "alternating electromagnetic field", "electromagnetic field" or "EM field" are synonymous. An electromagnetic field useful in the invention can be generated by various means well known in the art. A schematic illustration of exemplary setups are depicted respectively in FIG. 1. An electromagnetic field of a desired frequency and a desired field strength is generated by an electromagnetic wave source (3) which comprises one or more signal generators that are capable of generating electromagnetic waves, preferably sinusoidal waves, and preferably in the frequency range of 1,500 to 15,000 MHz and most preferably 10,000 to 12,800 MHz. Such signal generators are well known in the art. Signal generators capable of generating signal with a narrower frequency range can also be used. If desirable, a signal amplifier can also be used to increase the output signal, and thus the strength of the EM field.

The electromagnetic field can be applied to the culture by a variety of means including placing the yeast cells in close proximity to a signal emitter connected to a source of electromagnetic waves. The signal generator is connected to the signal emitter by cables such as coaxial cables that can transmit signals up to greater than or equal to 30 GHz. Typically, the yeast cells are placed in a container which is made of material that is not an electric conductor, such as but not limited to plastic, resin, glass, and ceramic.

In one embodiment, the electromagnetic field is applied by signal emitters in the form of electrodes (4) that are submerged in a culture of yeast cells (1). In a preferred embodiment, one of the electrodes is a metal plate which is placed on the bottom of a non-conducting container (2), and the other electrode comprises a plurality of wires or tubes so configured inside the container such that the energy of the electromagnetic field can be evenly distributed in the culture. The electrodes are preferably made of copper. For an upright culture vessel, the tips of the wires or tubes are placed within 3 to 30 cm from the bottom of the vessel (i.e., approximately 2% to 10% of the height of the vessel from the bottom). Table 1 provides exemplary set up for culturing the yeast cells of the invention.

TABLE 1

| height of culture medium in the non-conducting container (cm) | distance electrodes are placed from the bottom of the container (cm) | range for distance of the electrodes from the bottom (cm) |
| --- | --- | --- |
| 15 to 20 | 3 | 3 to 5 |
| 20 to 30 | 5 | 5 to 7 |
| 30 to 50 | 7 | 7 to 10 |
| 50 to 70 | 10 | 10 to 15 |
| 70 to 100 | 15 | 15 to 20 |
| 100 to 150 | 20 | 20 to 30 |
| 150 to 200 | 30 | 25 to 30 |

The number of electrodes used depends on both the volume of the culture and the diameter of the electrode. For example, for a culture having a volume of 10 liter or less, two or three electrodes having a diameter of between 0.5 to 2.0 mm can be used. For a culture volume of 10 to 100 liter of culture, the electrodes can have a diameter of 3.0 to 5.0 mm. For a culture volume of 100 to 1,000 liter, the electrodes can have a diameter of 6.0 to 15.0 mm. For a culture having a volume greater than 1,000 liter, the electrodes can have a diameter of between 20.0 to 25.0 mm.

5.1.3 Activation of Yeast Cells

According to the invention, the method for producing activated yeast cells of the invention comprises culturing yeast cells in the presence of at least two, three, four or five alternating electromagnetic (EM) fields.

The culture process can be initiated by inoculating 1,000 ml of medium with an inoculum of a selected yeast strain (such as one of those described in Section 5.1.1) such that the starting cell density of the culture is greater than about $10^5$ cells per ml. For example, Saccharomyces cerevisiae Hansen strain AS2.502 can be used. The starting culture can be used to seed larger scale culture. The culture is maintained initially at 28° C. to 32° C. for 22 to 30 hours prior to exposure to the EM field(s), typically at 30° C. for 28 hours.

The culturing process may preferably be conducted under conditions in which the concentration of dissolved oxygen is between 0.025 to 0.08 mol/m$^3$, preferably 0.04 mol/m$^3$. The oxygen level can be controlled by any conventional means known in the art, including but not limited to stirring and/or bubbling.

The culture is most preferably carried out in a liquid medium which contains sources of nutrients assimilable by the yeast cells. Table 2 provides an exemplary medium for culturing the yeast cells of the invention.

TABLE 2

| Medium Composition | Quantity |
| --- | --- |
| Sucrose or glucose | 20 g |
| Vitamin $B_{12}$ | 40 µg |
| Vitamin $B_6$ | 30 µg |
| Vitamin A | 50 µg |
| Vitamin C | 40 µg |
| Bovine calf serum | 35 ml |
| $KH_2PO_4$ | 0.20 g |
| $MgSO_4.7H_2O$ | 0.25 g |
| NaCl | 0.30 g |
| $CaSO_4.2H_2O$ | 0.20 g |
| $CaCO_3.5H_2O$ | 4.0 g |
| Peptone | 2.5 g |
| Autoclaved water | 1,000 ml |

The culturing medium is heated to 45° C. and cooled before adding the vitamin $B_{12}$, vitamin $B_6$, vitamin A, vitamin C and bovine calf serum.

In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and is preferably between about 0.2% and 2%. These carbon sources can be used individually, or several such carbon sources may be combined in the medium. Among the inorganic salts which can be incorporated in the culture media are the customary salts capable of yielding sodium, calcium, phosphate, sulfate, carbonate, and like ions. Non-limiting examples of nutrient inorganic salts are $KH_2PO_4$, $(NH_4)_2HPO_4$, $CaCO_3$, $MgSO_4$, NaCl, and $CaSO_4$.

It should be noted that the composition of the media provided in Table 2 is not intended to be limiting. The process can be scaled up or down according to needs. Various modifications of the culture medium may be made by those skilled in the art, in view of practical and economic considerations, such as the scale of culture and local supply of media components.

In certain embodiments, a series of at least two, three, four or five EM fields are applied to the culture of yeast cells, each having a different frequency within a stated range, and a different field strength within a stated range. The EM fields can be applied in any order and by any means known in the art, such as the apparatus described in Section 5.1.2. Although any of the following two, three or four EM fields can be applied, preferably, all five EM fields are applied.

For the first EM field, the frequency range is in the range of 10,081 to 10,090 MHz and the field strength is in the range of 230 to 250 mV/cm. The yeast culture is exposed to this first EM field at 30±2° C. for about 20 hours.

For the second EM field, the frequency range is in the range of 11,210 to 11,220 MHz and the field strength is in the range of 210 to 230 mV/cm. The yeast culture is exposed to this second EM field at 30±2° C. for about 8 hours.

For the third EM field, the frequency range is in the range of 12,141 to 12,150 MHz and the field strength is in the range of 245 to 265 mV/cm. The yeast culture is exposed to this third EM field at 30±2° C. for about 22 hours.

For the fourth EM field, the frequency range is in the range of 12,341 to 12,350 MHz and the field strength is in the range of 220 to 240 mV/cm. The yeast culture is exposed to this fourth EM field at 30±2° C. for about 8 hours.

For the fifth EM field, the frequency range is in the range of 12,781 to 12,790 MHz and the field strength is in the range of 280 to 300 mV/cm. The yeast culture is exposed to this fifth EM field at 30±2° C. for about 24 hours.

In less preferred embodiments, the yeast cells can be cultured by exposure to two, three or four of the above-mentioned EM fields in a different order. The yeast cells can remain in the same container and use the same set of electromagnetic wave generator and emitters when switching from one EM field to another EM field.

The cell density of the culture at the end of the activation process is typically greater than about $10^6$ to $10^9$ cells per ml (estimated by hematocytometer). The activated yeast cells may be recovered from the culture by various methods known in the art, and stored at a temperature below about 0° C. to 4° C. The activated yeast cells recovered from the liquid culture may be dried and stored in powder form. Preferably, the powder form of the yeast cells comprises greater than about $10^7$ to $10^{10}$ yeast cells per gram.

5.1.4 Conditioning of Yeast Cells

According to the invention, performance of the activated yeast cells can be optimized by culturing the activated yeast cells in the presence of an extract from the stomach (e.g., the gastric juice) of an animal with physiology similar to the subject to which the biological composition will be administered. The inclusion of this additional conditioning process allows the activated yeast cells to adapt to and endure the acidic environment of the subject's stomach. The method for conditioning activated yeast cells of the invention comprises culturing yeast cells in such materials in the presence of at least one EM field.

The culture process can be initiated by inoculating 1,000 ml of a conditioning medium with about 10 gram of dried activated yeasts containing about $10^{10}$ cells per gram (as prepared by the methods described in Section 5.1.3). An equivalent number of yeast cells in culture, preferably greater than $10^6$ to $10^9$ cells per ml, more preferably at $10^8$ cells per ml, can also be used as an inoculum. The conditioning medium comprises per 1,000 ml about 700 ml of gastric juice of an animal and about 300 ml of wild hawthorn juice. The process can be scaled up or down according to needs.

The gastric juice of an animal can be obtained from the stomach content of a freshly slaughtered animal. Although not essential, the animal is preferably kept under a clean environment, and fed a standard diet, preferably germ-free. For example, the content of the stomach of a 120-day old pig is mixed with 2,000 ml of distilled water, and allowed to settle without stirring for 6 hours. The clear liquid above is collected for use as the gastric juice used in the conditioning process. The gastric juice of a pig can be used to condition yeast cells for use in a variety of mammals, including humans. Other methods that can be used to collect the gastric juice include centrifugation or filtration of the mixture to remove debris and/or microorganisms. The gastric juice so obtained can be stored at 4° C. Preferably, the collection procedures and storage are carried out under sterile conditions.

The wild hawthorn juice is an extract of wild hawthorn fruits prepared by slicing the fruits and drying the slices in air, preferably to less than 8% moisture (commercial dryer can be used if necessary), crushing the dried fruits to less than 20 mesh, and mixing 1,500 ml of water per 500 gram of the crushed wild hawthorn. The mixture is then allowed to settle without stirring for 6 hours, and the clear liquid above is collected for use as the wild hawthorn juice used in the conditioning process. Other methods that can be used to collect the hawthorn juice include centrifugation or filtration of the mixture. Preferably, the collection procedures and storage are carried out under sterile conditions.

The activated yeast cells are conditioned by culturing in at least one of the following two EM fields which can be applied by the apparatus described in Section 5.1.2 or any means known in the art:

The first EM field has a frequency in the range of 12,341 to 12,350 MHz and a field strength in the range of 280 to 300 mV/cm. The temperature is maintained at 28° C. to 32° C., and typically at 30° C. The yeast culture is exposed to this first EM field for about 8 hours.

The second EM field has a frequency in the range of 12,781 to 12,790 MHz and a field strength in the range of 290 to 310 mV/cm. The temperature is maintained at 28° C. to 32° C., and typically at 30° C. The yeast culture is exposed to this second EM field for about 42 hours.

In a preferred embodiment, the activated yeast cells are conditioned by culturing in both of the above-mentioned EM fields. In less preferred embodiments, the yeast cells are conditioned in the two different EM fields in a different order. In other embodiments, a series of EM fields having field characteristics within the ranges stated above can be applied to condition the yeast cells. The yeast cells can remain in the same container and use the same set of electromagnetic wave generator and emitters when switching from one EM field to another EM field.

The cell density of the culture at the end of the activation process is typically greater than about $10^7$ to $10^{10}$ cells per ml (estimated by hematocytometer). The activated and conditioned yeast cells may be recovered from the culture by various methods known in the art, and stored at a temperature below about 0° C. to 4° C.

The activated and conditioned yeast cells can be used directly in a biological composition or used as a starter culture for large scale manufacturing. The activated and conditioned yeast cells recovered from the liquid culture may be dried and stored in powder form. Preferably, the powder form of the activated and conditioned yeast cells comprises greater than about $10^8$ to $10^{11}$ yeast cells per gram.

5.1.5 Large Scale Manufacturing

The present invention also encompasses methods of manufacturing of the biological compositions of the invention at a large scale. The activated and conditioned yeast cells as prepared by Sections 5.1.3 and 5.1.4 are propagated on a large scale to make the biological compositions of the invention. The method comprises culturing the yeast cells in the presence of one or more EM fields for a period of time, diluting the growing yeast cells with fresh medium, and repeating the process. The method can be carried out as a batch process or a continuous process.

In one preferred embodiment, a set of three containers (5, 6, 7) each comprising a set of electrodes for generating an electromagnetic field as described in Section 5.1.2 are set up each with 1,000 liters of a culture medium. See FIG. 2. The culture medium comprises nutrients assimilable by the yeast cells as shown in Table 3.

TABLE 3

| Material | Quantity |
| --- | --- |
| Wild hawthorn juice | 300 liters |
| Jujube juice | 300 liters |
| Wu wei zi juice | 300 liters |
| Soybean juice | 100 liters |

The wild hawthorn juice is an extract of fresh wild hawthorn fruits prepared by washing the fruits clean, drying the fruits in air or using a commercial dryer to less than 8% moisture, crushing the dried fruits to less than 20 mesh, and mixing the crushed wild hawthorn with water at a ratio of 400 liters of water per 100 kg of crushed fruits. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The jujube juice is an extract of fresh jujube fruits prepared by washing the fruits clean, drying the fruits to less than 8% moisture, crushing the dried fruits to less than 20 mesh, and mixing the crushed jujube with water at a ratio of 400 liters of water per 100 kg of crushed fruits. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The wu wei zi juice is an extract of fresh berries of *Schisandra chinensis* plant prepared by washing the berries, drying the fruits to less than 8% moisture, crushing the dried berries to less than 20 mesh, and mixing the crushed berries with water at a ratio of 400 liters of water per 100 kg of crushed berries. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The soybean juice is prepared by washing the soybeans, drying the soybeans to less than 8% moisture, crushing the soybeans to less than 20 mesh, and mixing the crushed soybeans with water. For 30 kg of soybeans, 130 liters of water is used. The mixture is then stirred continuously for 12 hours while the temperature is maintained at 28° C. to 30° C. The mixture is then centrifuged at 1,000 rpm to collect the supernatant which is used as described above. Preferably, the procedures are carried out under sterile conditions.

The first container is inoculated with activated or acti-vated and conditioned yeast cells as prepared by the methods of Sections 5.1.4 and 5.1.5. About 1,000 gram of dried yeast powder are added to 1,000 liter of culture medium. Each gram of the dried yeast powder comprises about $10^{10}$ yeast cells. Instead of dried yeast cells, an equivalent number of yeast cells in a liquid medium can also be used, preferably greater than about $10^6$ to $10^9$ cells per ml, more preferably about $10^7$ cells per ml.

The yeast cells in the first container (5) are then subjected to a series of two EM fields. For the first EM field, which can be applied by the apparatus described in Section 5.1.2, the frequency is in the range of 12,341 to 12,350 MHz and the field strength is in the range of 300 to 320 mV/cm. The yeast culture is exposed to this first EM field for about 8 hours. The yeast cells are then subjected to a second EM field having a frequency in the range of 12,781 to 12,790 MHz and a field strength in the range of 320 to 340 mV/cm. The yeast culture is exposed to this second EM field for about 12 hours. The yeast cells from the first container are then transferred to the second container which contains about 1,000 liter of the culture medium. In effect, the first yeast culture is diluted by about 50% with fresh culture medium.

In the second container (6), the yeast cells are again subjected to a series of two EM fields. The frequencies used in the second container are similar to those used in the first container but the field strengths are marginally lower. The first EM field has a frequency in the range of 12,341 to 12,350 MHz and a field strength in the range of 320 to 340 mV/cm. The yeast culture is exposed to this EM field for about 8 hours. The yeast cells are then subjected to a second EM field having a frequency in the range of 12,781 to 12,790 MHz and a field strength in the range of 330 to 350 mV/cm. The yeast culture is exposed to this second EM field for about 12 hours. The yeast cells from the second container are then transferred to the third container which contains yet another 1,000 liter of the culture medium. Again, the second yeast culture is diluted by about 50% with fresh culture medium.

In the third container (7), the yeast cells are again subjected to a series of two EM fields. The frequencies used in the third container are similar to those used in the first and second container but the field strengths are lower. The first EM field has a frequency in the range of 12,341 to 12,350 MHz and field strength in the range of 230 to 240 mV/cm. The yeast culture is exposed to this EM field for about 10 hours. The yeast cells are then subjected to a second EM field having a frequency in the range of 12,781 to 12,790 MHz and a field strength in the range of 220 to 240 mV/cm. The yeast culture is exposed to this EM field for about 22 hours.

The yeast cell culture resulting from the end of this stage can be used directly as an oral composition of the invention, or used to form other compositions encompassed by the invention.

The cell density of the culture at the end of the large scale manufacturing process is typically greater than about $10^8$ to $10^{10}$ cells per ml (estimated by hematocytometer). The concentration of yeast cells in the medium can be concentrated or diluted accordingly. In certain embodiments, the concentration of yeast cells in the medium is in the range of $10^3$ to $10^{10}$ cells per ml. In less preferred embodiments, the concentration of yeast cells in the medium is in the range of $10^3$ to $10^6$ cells per ml. In more preferred embodiments, the concentration of yeast cells in the medium is greater than $10^6$ to $10^{10}$ cells per ml. In most preferred embodiments, the concentration of yeast cells in the medium is in the range of $10^6$ to $5 \times 10^8$ cells per ml.

Other ingredients that enhance the healthful benefits, pharmacological properties and/or organoleptic characteristics of the composition can be added to the yeast cell culture. To maintain viability and freshness of the composition, it is preferred that the various downstream and packaging process be carried out below room temperature, and preferably at 0° C. to 4° C. In one embodiment, the yeast cell culture can be packaged in liquid containers.

In another embodiment, the activated and conditioned yeast cells can be dried as follows. The yeast cell culture is first centrifuged under 75 to 100 g for 10 to 20 minutes to remove the supernatant. The residue which may contain up to 85% moisture is dried in a first dryer at a temperature not exceeding 60±2° C. for a period of 5 minutes so that yeast cells quickly became dormant. The yeast cells were then sent to a second dryer and dried at a temperature not exceeding 65±2° C. for a period of about 8 minutes to further remove at least 10%, at least 20%, at least 30%, at least 40%, at least 50%, at least 60%, at least 70%, at least 80%, at least 90%, at least 95%, at least 98%, or at least 99% of water. For example, the yeast cells may be dried to remove at least 88% of water so the dried yeast cells may contain up to 12% moisture.

After cooling to room temperature, the dried yeast cells can be packaged by standard pharmaceutical methods in various solid dosage form, each containing a predetermined amount of the dried material. In a preferred embodiment, the dried material comprises about $10^5$ to $10^{11}$ cells per gram. In a more preferred embodiment, the dried material comprises about $10^8$ to $5\times10^{10}$ cells per gram. In a most preferred embodiment, the dried material comprises about $5\times10^8$ cells per gram.

In general, the compositions are prepared by uniformly and intimately admixing the active ingredient with liquid carriers or finely divided solid carriers.

5.1.6 Preferred Embodiments

In one preferred embodiment, the invention provides a method for preparing a biological composition comprising activated and conditioned yeast cells, said method comprising in any order the steps of:
  (a) culturing the yeast cells in a first electromagnetic field having a frequency at 10,088 MHz and a field strength of 243 mV/cm;
  (b) culturing the yeast cells in a second electromagnetic field having a frequency at 11,214 MHz and a field strength of 228 mV/cm;
  (c) culturing the yeast cells in a third electromagnetic field having a frequency at 12,142 MHz and a field strength of 257 mV/cm;
  (d) culturing the yeast cells in a fourth electromagnetic field having a frequency at 12,346 MHz and a field strength of 216 mV/cm; and
  (e) culturing the yeast cells in a fifth electromagnetic field having a frequency at 12,786 MHz and a field strength of 283 mV/cm;

and after the last of the first five steps, the following steps in any order:
  (f) culturing the yeast cells in a liquid medium comprising wild hawthorn juice and gastric juice of a mammal in a sixth electromagnetic field having a frequency at 12,346 MHz and a field strength of 284 mV/cm; and
  (g) culturing the yeast cells in a liquid medium comprising wild hawthorn juice and gastric juice of a mammal in a seventh electromagnetic field having a frequency at 12,786 MHz and a field strength of 306 mV/cm.

The activated and conditioned yeast cells obtained at the conclusion of this method is encompassed by the invention. Preferably, the yeast cells are *Saccharomyces cerevisiae* Hansen strain AS2.502. These yeast cells can be used in the following method of further expanding number of activated and conditioned yeast cells.

In another preferred embodiment, the invention provides a method of mass producing a biological composition comprising activated and conditioned yeast cells, said method comprising culturing the activated and conditioned yeast cells prepared by the preferred embodiment described above in this section, in a medium comprising wild hawthorn juice, jujube juice, wu wei zi juice, and soybean juice, and in the presence of one or more series of electromagnetic fields. Each series of EM fields comprises two EM fields in the order stated:
  (h) an eighth electromagnetic field or series of electromagnetic fields having a frequency at 12,346 MHz and a field strength in the range of 230 to 340 mV/cm, preferably at three fields strengths, e.g., in the order of 311 mV/cm, 323 mV/cm, and 236 mV/cm; and
  (i) a ninth electromagnetic field or series of electromagnetic fields having a frequency at 12,786 MHz and a field strength in the range of 220 to 350 mV/cm, preferably at three fields strengths, e.g., in the order of 322 mV/cm, 342 mV/cm, and 234 mV/cm.

The series may be repeated several times, such as three times, each time using a slightly lower field strength.

5.2 Methods of Uses 5.2.1 Uses In Subjects with Ovarian Cancer

The present invention further provides methods of use of the biological compositions of the invention. In one embodiment, the biological composition is used as a medicament for treatment of ovarian cancer. In another embodiment, the biological composition is used as a dietary supplement, health food, or health drink. The methods comprise administering an effective amount of the biological composition to a subject in need. The biological composition may be administered orally, in liquid or solid form, or enterally through a feeding tube. As used herein, the term "an effective amount" means an amount sufficient to provide a therapeutic or healthful benefit in the context of ovarian cancer.

According to the invention, the biological composition can produce a healthful benefit in a subject suffering from ovarian cancer. Preferably, the subject is a human being. The subject in need is one who is diagnosed with ovarian cancer, with or without metastasis, at any stage of the disease (e.g., TX, T0, Tis, T1, T2, T3, T4, NX, N0, N1, MX, M0 and M1). As used herein, the term "ovarian cancer" includes but is not limited to serous carcinoma and those arising from the celomic epithelium, specialized stroma, and germ cell layer or unfertilized ovum.

The subject may be a ovarian cancer patient who is receiving concurrently other treatment modalities against the ovarian cancer. The subject can be a ovarian cancer patient who had undergone a regimen of treatment (e.g., chemotherapy and/or radiation) and whose cancer is regressing. The subject may be a ovarian cancer patient who had undergone a regimen of treatment (e.g., surgery) and who appears to be clinically free of the ovarian cancer. The biological composition of the invention can be administered adjunctively with any of the treatment modalities, such as but not limited to chemotherapy, radiation, and/or surgery. For example, the biological composition can be used in combination with one or more chemotherapeutic or immunotherapeutic agents, such as epoetin alfa (Procrit®, Epogen®) and amifostine (Ethyol; Alza Pharmaceuticals, Palo Alto, Calif./US Bioscience, West Conshohocken, Pa.). The biological composition can also be used after other regimen(s) of treatment is concluded.

The subject may be one who has not yet been diagnosed with ovarian cancer but are predisposed to or at high risk of developing ovarian cancer as a result of genetic factors and/or environmental factors. The subject may also be one who displays characteristics that are associated with a high risk of ovarian cancer, such as nodules detected by computer tomographic scanning or suspect cells in biopsy and/or body fluids.

Depending on the subject, the therapeutic and healthful benefits range from inhibiting or retarding the growth of the ovarian cancer and/or the spread of the ovarian cancer to other parts of the body (i.e., metastasis), palliating the symptoms of the cancer, improving the probability of survival of the subject with the cancer, prolonging the life expectancy of the subject, improving the quality of life of the subject, and/or reducing the probability of relapse after a successful course of treatment (e.g., surgery, chemotherapy or radiation). The symptoms associated with ovarian cancer include abdominal pain, abdominal swelling, bloating or dyspepsia, pelvic pressure, weight gain or loss, abnormal menstrual cycles, increased abdominal girth, vaginal bleeding, excessive hair, and increased urinary frequency or urgency.

In particular, the invention provides a method for retarding the growth of ovarian cancer cells in a subject, such as a human, comprising administering orally to the subject a biological composition of the invention. The invention also provide a method for prolonging the time of survival of a subject inflicted with ovarian cancer, preferably a human patient, comprising administering orally to the subject a biological composition of the invention.

The effective dose will vary with the subject treated. The effective dose for the subject will also vary with the condition to be treated and the severity of the condition to be treated. The dose, and perhaps the dose frequency, will also vary according to the age, body weight, and response of the individual subject. In general, the total daily dose range of activated and conditioned yeast cells for a subject inflicted with ovarian cancer is from about $10^5$ to $10^{11}$ cells per day; preferably, about $10^8$ to $5 \times 10^{10}$ cells per day; more preferably, about $2 \times 10^9$ cells per day in powder form or $9 \times 10^8$ to $1 \times 10^{10}$ cells per day in liquid preparations, administered in single or divided doses orally. The length of time for a course of treatment should be at least 1 week, at least 2 weeks, at least 3 weeks, at least 4 weeks, at least 5 weeks, at least 7 weeks, at least 10 weeks, at least 13 weeks, at least 15 weeks, at least 20 weeks, at least 6 months, or at least 1 year. It may be necessary to use dosages outside these ranges in some cases as will be apparent to those skilled in the art. In certain embodiments, the oral compositions can be administered for a period of time until the symptoms and/or infection of the patients by the bacteria and viruses are under control, or when the disease has regressed partially or completely. For use as a dietary supplement, the total daily dose range should be from about $10^5$ to $10^{11}$ cells per day; preferably, about $5 \times 10^7$ to $5 \times 10^9$ cells per day. The oral compositions can be administered as a dietary supplement for as long as 6 months, or in accordance with recommended length of use under the Dietary Supplement Health and Education Act (DSHEA) or other government or industry guidelines. Further, it is noted that the nutritionist, dietician, clinician or treating physician will know how and when to interrupt, adjust, or terminate use of the biological composition as a medicament or dietary supplement in conjunction with individual patient response.

The effect of the biological compositions of the invention on development and progression of ovarian cancer can be monitored by any methods known to one skilled in the art, including but not limited to measuring: a) changes in the size and morphology of the tumor using imaging techniques such as a computed tomographic (CT) scan or a sonogram; and b) changes in levels of biological markers of risk for ovarian cancer.

5.2.2 Formulations

The biological compositions of the present invention comprise activated and conditioned live yeast cells prepared as described above in Section 5.1, as active ingredient, and can optionally contain a pharmaceutically acceptable carrier or excipient, and/or other ingredients provided that these ingredients do not kill or inhibit the yeast cells. Other ingredients that can be incorporated into the biological compositions of the present invention, may include, but are not limited to, herbs (including traditional Chinese medicine products), herbal extracts, vitamins, amino acids, metal salts, metal chelates, coloring agents, flavor enhancers, preservatives, and the like.

Any dosage form may be employed for providing the subject with an effective dosage of the oral composition. Dosage forms include tablets, capsules, dispersions, suspensions, solutions, and the like. In one embodiment, compositions of the present invention suitable for oral administration may be presented as discrete units such as capsules, cachets, or tablets, each containing a predetermined amount of activated and conditioned yeast cells, as a powder or granules or as a solution or a suspension in an aqueous liquid, a non-aqueous liquid, an oil-in-water emulsion, or a water-in-oil liquid emulsion. In general, the compositions are prepared by uniformly and intimately admixing the active ingredient with liquid carriers or finely divided solid carriers or both, and then, if necessary, shaping the product into the desired presentation. Such products can be used as pharmaceuticals or dietary supplements, depending on the dosage and circumstances of its use.

The oral compositions of the present invention may additionally include binding agents (e.g., pregelatinized maize starch, polyvinylpyrrolidone or hydroxypropyl methylcellulose); binders or fillers (e.g., lactose, pentosan, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets or capsules can be coated by methods well known in the art.

Liquid preparations for oral administration can take the form of, for example, solutions, syrups or suspensions, or they can be presented as a dry product for constitution with water or other suitable vehicle before use. The temperature of the liquid used to reconstitute the dried product should be less than 65° C. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). As described below, the preparations can also be made to resemble foods or beverages, containing buffer salts, flavoring, coloring and sweetening agents as appropriate. In certain embodiments, the oral composition is a cell suspension comprising about $10^3$ to $10^{10}$ cells per ml. The oral composition can be produced by diluting or concentrating the yeast culture medium produced by the method of Section 5.1.5 as required. In less preferred embodiments, the oral composition is a cell suspension containing about $10^3$ to $10^6$ cells per ml. In more preferred embodiments, the oral composition is a cell suspension containing greater than about $10^6$ to $10^{10}$ cells per ml. In most preferred embodiments, the oral composition is a cell suspension containing about $10^6$ to $5 \times 10^8$ cells per ml. The oral composition can be formulated as a health drink and packaged in liquid containers, each containing a predetermined amount of the liquid yeast culture. Standard methods of quality control and packaging are applied to produce in one embodiment of the invention, oral compositions packaged in liquid containers each comprising about 1 ml, 2 ml, 3 ml, 4 ml, 5 ml, 10 ml, 15 ml, 20 ml, 30 ml, 40 ml, 50 ml, 75 ml, 100 ml, 150 ml, 200 ml, 250 ml, 500 ml, 750 ml, or 1,000 ml of the live yeast cells. The number of container to be taken each day to obtain the total daily dose in a subject depends on the number of activated and conditioned yeast cells contained within each container. For example, a container may comprise 50 ml of liquid with $10^7$ cells per ml and when a total daily dose of about $2\times10^9$ cells per day is desired, a subject can drink 4 containers per day to obtain the desired total daily dose.

Generally, because of their ease of administration, tablets and capsules represent the most advantageous oral dosage unit form, in which case solid pharmaceutical carriers as described above are employed. In a preferred embodiment, the composition is a capsule. The capsules can be formulated by any commercially available methods. In certain embodiments, the composition is a capsule containing 5 mg, 10 mg, 15 mg, 20 mg, 25 mg, 30 mg, 40 mg, 50 mg, 75 mg, 100 mg, 150 mg, 200 mg, 300 mg, 400 mg, 500 mg, 600 mg, 700 mg, 800 mg, 900 mg, 1.0 gram, 1.25 gram, 1.5 gram, or 2.0 gram of live yeast cells in powder form. The powder in the capsule comprises about $10^5$ to about $10^{11}$ cells per gram; more preferably, about $10^8$ to $5\times10^{10}$ cells per gram; and most preferably, about $5\times10^8$ cells per gram. The number of capsule to be taken each day to obtain the total daily dose in a subject depends on the number of activated and conditioned yeast cells contained within each capsule. For example, a capsule may comprise about 500 mg of powder with $5\times10^8$ cells per gram. To achieve a total daily dose of about $2\times10^9$ cells per day, a subject can take two capsules at a time for four times per day.

In another embodiment, the biological compositions comprising activated and conditioned yeast cells can be added directly to foods so that an effective amount of yeast cells is ingested during normal meals. Any methods known to those skilled in the art may be used to add to or incorporate the biological compositions into natural or processed foods, provided that the activated and conditioned yeast cells remain viable. Preferably, the nutritional compositions of the invention are made and stored under conditions, such as temperature, from about 0° C. to 4° C. As used herein, the term "food" broadly refers to any kind of material, liquid or solid, that is used for nourishing an animal, and for sustaining normal or accelerated growth of an animal including humans. Many types of food products or beverages, such as but not limited to, fruit juice, herbal extracts, tea-based beverages, dairy products, soybean product (e.g., tofu), and rice products, can be used to form nutritional compositions comprising the activated and conditioned yeast cells of the invention.

The invention is further defined by reference to the following example describing in detail the animal trials conducted to study the efficacy and safety of activated and conditioned yeast cells of the invention.

6. EXAMPLE

The following example illustrates the benefit of a biological composition of the invention in a mouse model of human ovarian cancer. The growth of the tumor in the mice was studied.

Numerous animal studies have reported the use of orthotopic transplant technique in female mouse models to study the treating of ovarian cancer. See, for example, Animals for Experiments and Experimental Techniques, Chinese Medical Publisher, 1997. The use of orthotopic transplant technique has been highly successful in the development of mouse models of human ovarian cancer.

The human ovarian cancer sample is carefully selected before, during, and after surgery in order to ensure transplant occurred at the equivalent position in the mouse. The ovarian cancer sample is obtained from patients who have not received any radiation, chemotherapy, or immune enhancement treatment.

The biological composition comprising $10^8$ cells per ml of activated and conditioned yeast cells of the strain *Saccharomyces cerevisiae* Hansen strain AS2.502 was prepared by the methods described in Section 5.1 and subsections therein.

6.1 Animal Preparation

The animals used to generate the ovarian cancer cells for the experiments were first generation female offspring of crosses between AKR inbred mouse and Beijing white mouse (obtainable from the Chinese Academy of Military Medical Sciences, Beijing, China), having an average body weight of about 20 to 22 gram. Fresh ovarian tumor cells (obtainable from the Cancer Institute, Chinese Academy of Medical Sciences, Beijing, China) were divided into sections of size 1–2 mm$^3$ and immediately stored in RPMI-1640 suspension after removal from the human patient.

The mouse were starved for 24 hours before the surgery. The animals were generally anaesthetized. The barbiturates was first diluted in saline and then injected at 0.3 to 0.4 ml per animal, or 30 mg per kg body weight, into the abdomen of the mice. Under sterile conditions, a 1 cm long opening in the body cavity was cut along the right rib of the mice for engraftment of the tumor. About $10^6$ units of tumor cells (about 2 mg tumor pieces per ml culture medium) were transplanted. Afterwards, the opening was sutured and the mice were put back into the cage. The animals were allowed to grow for three to five weeks or when the tumor grows to about 1 to 2 cm$^3$ in size. The animals that showed robust growth of the tumor were used as donors. The tumor was removed from a donor mouse and minced aseptically in 4 ml of Hank's solution to form a cell suspension. About $10^6$ units of tumor cells (about 0.2 ml cell suspension) were transplanted into a healthy batch of mice.

6.2 Experimental Design

The mice injected with tumor cells were immediately divided into 4 experimental groups of ten mice per group and one control group. The four experimental groups were triplicated (i.e., using a total of 120 mice in the experimental groups). In group AY, the mice received 0.3 ml of the biological composition once per day. In group NY, the mice received 0.3 ml of the untreated yeast cells once per day. In group TSPA, the mice were injected intravenously with 1.5 mg of thiotepa (TSPA) per kg body weight per day. In group CK1, the mice received 0.3 ml of physiological saline once per day. A fifth group of mice, group CK2, which did not receive tumor cells, was given 0.3 ml of physiological saline per day.

The mice received the biological compositions, untreated yeast cells, TSPA or saline on the same day as the tumor cells were transplanted. The mice in group CK2 also started receiving saline on the same day as the other four groups. The biological compositions, untreated yeast cells and saline were administered orally by a feeding tube and the TSPA by intravenous injection for 30 consecutive days. On the 31st day from tumor inoculation, the mice were sacrificed. The weight of the mice and the weight of the tumor were determined by standard techniques.

6.3 Results

Table 4 shows the differences in the body weight and the weight of tumor of the mice in the various treatment and control groups.

TABLE 4

| Group | mean weight of mice and standard deviation (g) | mean weight of tumor nodules and standard deviation (mg) |
| --- | --- | --- |
| AY | 23 ± 1.6 | 0.7 ± 0.5 |
| NY | 20 ± 2.5 | 3.9 ± 1.3 |
| TSPA | 21 ± 2.1 | 3.1 ± 0.8 |
| CK1 | 21 ± 2.2 | 3.7 ± 1.4 |
| CK2 | 23 ± 2.7 | not applicable |

The mice bearing ovarian cancer cells that received 0.3 ml of the biological composition of the invention (group AY) showed the least deviation in body weight as compared to healthy mice not injected with tumor cells (group CK2). The mice in group AY also had less tumor mass as compared to mice that did not receive treatment (group CK1) as well as the mice in group NY (0.3 ml of untreated yeast cells per day) and the mice in group TSPA (1.5 mg of thiotepa per kg body weight per day).

7. EXAMPLE

The following example illustrates the benefit of a biological composition of the invention in a mouse model of human ovarian cancer. The growth of the tumor in the mice was studied.

The biological composition comprising $10^8$ cells per ml of activated and conditioned yeast cells of the strain *Saccharomyces cerevisiae* Hansen strain AS2.502 was prepared by the methods described in Section 5.1 and subsections therein.

7.1 Animal Preparation

The animals were prepared in a similar manner as described in Section 6.1.

7.2 Experimental Design

The mice injected with tumor cells were kept for 2 weeks and then were divided into 4 experimental groups of ten mice per group and one control group. The four experimental groups were triplicated (i.e., using a total of 120 mice in the experimental groups). In group 2AY, the mice received 0.3 ml of the biological composition once per day. In group 2NY, the mice received 0.3 ml of the untreated yeast cells once per day. In group 2TSPA, the mice were injected intravenously with 1.5 mg of thiotepa (TSPA) per kg body weight per day. In group 2CK1, the mice received 0.3 ml of physiological saline once per day. A fifth group of mice, group 2CK2, which did not receive tumor cells, was given 0.3 ml of physiological saline per day.

The mice received the biological compositions, untreated yeast cells, TSPA or saline on the same day as the tumor cells were transplanted. The mice in group 2CK2 also started receiving saline on the same day as the other four groups. The biological compositions, untreated yeast cells and saline were administered orally by a feeding tube and the TSPA by intravenous injection for 30 consecutive days. The mice were observed over 6 months from the day of tumor inoculation and survival was recorded. The weight of the mice and the weight of the tumor were determined by standard techniques.

7.3 Results

Table 5 shows the number of mice in the various treatment and control group that survived the tumor injection over a period of 6 months. Each of the 30 mice in each group received 30 consecutive days of either untreated yeast cells, TSPA, saline or biological compositions of the invention.

Table 6 shows the weight of the mice that survived and the weight of their tumors in the various treatment and control groups.

TABLE 5

| | Number of live animals remaining in the groups after 30 days of treatment | | | | |
| --- | --- | --- | --- | --- | --- |
| Time after cessation of treatment | Group 2AY | Group 2NY | Group 2TSPA | Group 2CK1 | Group 2CK2 |
| 0 month | 30 | 30 | 30 | 30 | 30 |
| 1 month | 30 | 12 | 24 | 13 | 30 |
| 2 months | 30 | 2 | 7 | 2 | 30 |
| 3 months | 30 | 0 | 2 | 0 | 30 |
| 4 months | 30 | 0 | 0 | 0 | 30 |
| 5 months | 30 | 0 | 0 | 0 | 30 |
| 6 months | 30 | 0 | 0 | 0 | 30 |

TABLE 6

| Group | mean weight of mice and standard deviation (g) | mean weight of tumor nodules and standard deviation (mg) |
| --- | --- | --- |
| 2AY | 20.0 ± 4.1 | 36.3 ± 17 |
| 2NY | all animals dead | all animals dead |
| 2TSPA | all animals dead | all animals dead |
| 2CK1 | all animals dead | all animals dead |
| 2CK2 | 20.0 ± 3.2 | not applicable |

The mice bearing ovarian cancer cells that received 0.3 ml of the biological composition of the invention (group 2AY) survived for more than 6 months and the tumor never reoccurred. On the contrary, the mice in group 2NY (0.3 ml of untreated yeast cells per day), group 2TSPA (1.5 of thiotepa per kg body weight per day) and group 2CK1 (0.3 ml of saline per day) all died during the experiment.

As in Example 6, the mice bearing ovarian cancer cells that received 0.3 ml of the biological composition of the invention (group 2AY) showed the least deviation in the weight of mice as compared to healthy mice not injected with tumor cells (group 2CK2).

8. EXAMPLE

The following example illustrates the benefit of a biological composition of the invention in a $C_{57}BL$ mouse model of human ovarian cancer. The growth of the tumor in the mice was studied.

The biological composition comprising $10^8$ cells per ml of activated and conditioned yeast cells of the strain *Saccharomyces cerevisiae* Hansen strain AS2.502 was prepared by the methods described in Section 5.1 and subsections therein

8.1 Animal Preparation

The animals used to generate the ovarian cancer cells for the experiments were female $C_{57}BL$ mouse (obtainable from the Chinese Academy of Military Medical Sciences, Beijing, China), six weeks old, having an average body weight of about 18 to 20 gram. Detailed description of the use of $C_{57}BL$ mice can be found in Roby K. F. et al., 2000, *Carcinogenesis* 21(4):585-91, which is incorporated herein by reference in its entirety. Ovarian tumor cells (cell line obtainable from the Cancer Institute, Chinese Academy of Medical Sciences, Beijing, China) were injected subcutaneously into the $C_{57}BL$ mice. The number of tumor cells injected was about $10^6$ units per mouse in a 0.2 ml culture suspension.

8.2 Experimental Design

The mice injected with tumor cells were kept for 5 days and then were divided into 4 experimental groups of ten mice per group and one control group. The four experimental groups were triplicated (i.e., using a total of 120 mice in the experimental groups). In group AY, the mice received 0.3 ml of the biological composition once per day. In group NY, the mice received 0.3 ml of the untreated yeast cells once per day. In group CTX, the mice were injected subcutaneously with 30 mg of cyclophosphamide (CTX), per kg body weight per day. In group CK1, the mice received 0.3 ml of physiological saline once per day. A fifth group of mice, group CK2, which did not receive tumor cells, was given 0.3 ml of physiological saline per day.

The mice received the biological compositions, untreated yeast cells, CTX or saline on the same day as the tumor cells were transplanted. The mice in group CK2 also started receiving saline on the same day as the other four groups. The biological compositions, untreated yeast cells and saline were administered orally by a feeding tube and the CTX by subcutaneous injection for 30 consecutive days. On the 31st day from tumor inoculation, the mice were sacrificed. The weight of the mice and the weight of the tumor were determined by standard techniques.

8.3 Results

Table 7 shows the differences in the body weight and the weight of tumor of the mice in the various treatment and control groups.

TABLE 7

| Group | mean weight of mice and standard deviation (g) | mean weight of tumor nodules and standard deviation (g) |
|---|---|---|
| AY | 21 ± 2.7 | 0.7 ± 0.6 |
| NY | 18 ± 2.3 | 4.7 ± 1.6 |
| CTX | 20 ± 2.3 | 3.3 ± 1.4 |
| CK1 | 19 ± 2.4 | 4.2 ± 1.9 |
| CK2 | 22 ± 2.5 | not applicable |

The mice bearing ovarian cancer cells that received 0.3 ml of the biological composition of the invention (group AY) showed the least deviation in the weight of mice as compared to healthy mice not injected tumor cells (group CK2). The mice of group AY also had less tumor mass as compared to mice that did not receive treatment (group CK1) as well as the mice in group NY (0.3 ml of untreated yeast cells per day) and the mice in group CTX (30 mg of cyclophosphamide per kg body weight per day).

9. EXAMPLE

The following example illustrates the benefit of a biological composition of the invention in a $C_{57}BL$ mouse model of human ovarian cancer. The survival time of mice after tumor injection and treatment was studied.

The biological composition comprising $10^8$ cells per ml of activated and conditioned yeast cells of the strain *Saccharomyces cerevisiae* Hansen strain AS2.502 was prepared by the methods described in Section 5.1 and subsections therein

9.1 Animal Preparation

The animals were prepared in a similar manner as described in Section 8.1.

9.2 Experimental Design

The mice injected with tumor cells were kept for 5 days and then were divided into 4 experimental groups of ten mice per group and one control group. The four experimental groups were triplicated (i.e., using a total of 120 mice in the experimental groups). In group 2AY, the mice received 0.3 ml of the biological composition once per day. In group 2NY, the mice received 0.3 ml of the untreated yeast cells once per day. In group 2CTX, the mice were injected subcutaneously with 305 mg of cyclophosphamide (CTX) per kg body weight per day. In group 2CK1, the mice received 0.3 ml of physiological saline once per day. A fifth group of mice, group 2CK2, which did not receive tumor cells, was given 0.3 ml of physiological saline per day.

The mice received the biological compositions, untreated yeast cells, CTX or saline on the same day as the tumor cells were transplanted. Mice in group 2CK2 also started receiving saline on the same day as the other four groups. The biological compositions, untreated yeast cells and saline were administered orally by a feeding tube and the CTX by subcutaneous injection for 30 consecutive days. The mice were observed over 6 months from the day of tumor inoculation and survival was recorded. The weight of the mice and the weight of the tumor were determined by standard techniques.

9.3 Results

Table 8 shows the number of mice in the various treatment and control group that survived the tumor injection over a period of 6 months. Each of the 30 mice in each group received 30 consecutive days of either untreated yeast cells, CTX, saline or biological compositions of the invention. Table 9 shows the weight of the mice that survived and the weight of their tumors in the various treatment and control groups.

TABLE 8

Number of live animals remaining in the groups after 30 days of treatment

| Time after cessation of treatment | Group 2AY | Group 2NY | Group 2CTX | Group 2CK1 | Group 2CK2 |
|---|---|---|---|---|---|
| 1 month | 30 | 29 | 30 | 27 | 30 |
| 2 months | 30 | 11 | 30 | 7 | 30 |
| 3 months | 30 | 0 | 23 | 0 | 30 |
| 4 months | 30 | 0 | 14 | 0 | 30 |
| 5 months | 30 | 0 | 9 | 0 | 30 |
| 6 months | 30 | 0 | 0 | 0 | 30 |

TABLE 9

| Group | mean weight of mice and standard deviation (g) | mean weight of tumor nodules and standard deviation (mg) |
|---|---|---|
| 2AY | 23 ± 2.4 | 133.7 ± 14.7 |
| 2NY | all animals dead | all animals dead |
| 2CTX | all animals dead | all animals dead |
| 2CK1 | all animals dead | all animals dead |
| 2CK2 | 23 ± 2.9 | not applicable |

The mice bearing ovarian cancer cells that received 0.3 ml of the biological composition of the invention (group 2AY) survived for more than 6 months and the tumor never reoccurred. On the contrary, the mice in group 2NY (0.3 ml of untreated yeast cells per day), group 2CTX (30 mg of cyclophosphamide per kg body weight per day) and group 2CK1 (0.3 ml of saline per day) all died during the experiment.

As in Example 8, the mice bearing ovarian cancer cells that received 0.3 ml of the biological composition of the invention (group 2AY) showed the least deviation in the weight of mice as compared to healthy mice not injected with tumor cells (group 2CK2).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings. Such modifications are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

What is claimed is:

1. A method of treating yeast cells, comprising at least two steps selected from the group consisting of:
   a. culturing yeast cells in a first electromagnetic field having a frequency in the range of 10,081 to 10,090 Mhz and a field strength in the range of 230 to 250 mV/cm;
   b. culturing the yeast cells in a second electromagnetic field having a frequency in the range of 11,210 to 11,220 MHz and a field strength in the range of 210 to 230 mV/cm;
   c. culturing the yeast cells in a third electromagnetic field having a frequency in the range of 12,141 to 12,150 MHz and a field strength in the range of 245 to 265 mV/cm;
   d. culturing the yeast cells in a fourth electromagnetic field having a frequency in the range of 12,341 to 12,350 MHz and a field strength in the range of 220 to 240 mV/cm; and
   e. culturing the yeast cells in a fifth electromagnetic field having a frequency in the range of 12,781 to 12,790 MHz and a field strength in the range of 280 to 300 mV/cm, and
   wherein said method further comprises the step of recovering the cultured yeast cells.

2. A method of treating yeast cells, comprising at least two steps selected from the group consisting of:
   a. culturing yeast cells in a first electromagnetic field having a frequency in the range of 10,081 to 10,090 MHz and a field strength in the range of 230 to 250 mV/cm;
   b. culturing the yeast cells in a second electromagnetic field having a frequency in the range of 11,210 to 11,220 MHz and a field strength in the range of 210 to 230 mV/cm;
   c. culturing the yeast cells in a third electromagnetic field having a frequency in the range of 12,141 to 12,150 MHz and a field strength in the range of 245 to 265 mV/cm;
   d. culturing the yeast cells in a fourth electromagnetic field having a frequency in the range of 12,341 to 12,350 MHz and a field strength in the range of 220 to 240 mV/cm; and
   e. culturing the yeast cells in a fifth electromagnetic field having a frequency in the range of 12,781 to 12,790 MHz and a field strength in the range of 280 to 300 mV/cm,
   wherein said method further comprising at least one step selected from the group consisting of:
   f. culturing the yeast cells in a liquid medium comprising wild hawthorn juice and gastric juice of a mammal in a sixth electromagnetic field having a frequency in the range of 12,341 to 12,350 MHz and a field strength in the range of 280 to 300 mV/cm; and
   g. culturing the yeast cells in a liquid medium comprising wild hawthorn juice and gastric juice of a mammal in a seventh electromagnetic field having a frequency in the range of 12,781 to 12,790 MHz and a field strength in the range of 290 to 310 mV/cm, and
   wherein said method further comprises the step of recovering the cultured yeast cells.

3. The method of claim 2, further comprising before the recovering step the following steps, which can be carried out in any order:
   h. culturing the yeast cells in a first liquid medium and an eighth electromagnetic field or series of electromagnetic fields having a frequency in the range of 12,341 to 12,350 MHz and a field strength in the range of 230 to 340 mV/cm; and
   i. culturing the yeast cells in a second liquid medium and a ninth electromagnetic field or series of electromagnetic fields having a frequency in the range of 12,781 to 12,790 MHz and a field strength in the range of 220 to 350 mV/cm,
   wherein the first and second liquid mediums each comprises wild hawthorn fruit juice, jujube fruit juice, wu wei zi berry juice, and soybean juice.

4. The method of claim 1, wherein the yeast cells to be treated are cells of *Saccharomyces*.

5. The method of claim 1, wherein the yeast cells to be treated are cells of *Saccharomyces cerevisiae* AS2.502.

6. The method of claim 2 or 3, wherein the yeast cells to be treated are cells of *Saccharomyces*.

7. The method of claim 2 or 3, wherein the yeast cells to be treated are cells of *Saccharomyces cerevisiae* AS2.502.

8. The method of claim 2 or 3, further comprising before the recovering step the following steps:
   j. drying the yeast cells at a temperature not exceeding 65° C. for a period of time, wherein the yeast cells become dormant; and
   k. drying the yeast cells at a temperature not exceeding 70° C. for a period of time to reduce the moisture content to below 5%.

* * * * *

UNITED STATES PATENT AND TRADEMARK OFFICE
CERTIFICATE OF CORRECTION

PATENT NO. : 7,204,986 B2  Page 1 of 1
APPLICATION NO. : 10/460246
DATED : April 17, 2007
INVENTOR(S) : Ling Yuk Cheung It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (309) days Delete the phrase "by 309 days" and insert -- by 360 days --

Signed and Sealed this

Ninth Day of October, 2007

JON W. DUDAS
*Director of the United States Patent and Trademark Office*